United States Patent
Sbarra et al.

[11] 4,111,200
[45] Sep. 5, 1978

[54] EYE DROP DISPENSER

[76] Inventors: Frank Sbarra, c/o George Spector, 3615 Woolworth Bldg., 233 Broadway; George Spector, 3615 Woolworth Bldg., 233 Broadway, both of, New York, N.Y. 10007

[21] Appl. No.: 639,412

[22] Filed: Dec. 10, 1975

[51] Int. Cl.² ............................................. A61M 1/00
[52] U.S. Cl. ................................... 128/233; 128/249
[58] Field of Search ............... 128/207, 233, 249, 260; 222/553, 548, 209

[56] References Cited
U.S. PATENT DOCUMENTS

| | | | |
|---|---|---|---|
| 1,603,727 | 10/1926 | Vilas | 128/249 |
| 2,589,178 | 3/1952 | Wintle, Jr. | 128/249 |
| 2,626,606 | 1/1953 | Campbell | 128/249 |
| 2,754,821 | 7/1956 | Burbig et al. | 128/249 |
| 2,924,393 | 2/1960 | Robert | 222/553 X |
| 3,006,514 | 10/1961 | Collins | 222/553 |
| 3,225,970 | 12/1965 | Rooney | 222/484 |
| 3,409,009 | 11/1968 | Vasse | 128/249 |

*Primary Examiner*—John D. Yasko

[57] ABSTRACT

An eye drop designed to facilitate dispensing an exact number of drops into the center of an eye.

2 Claims, 5 Drawing Figures

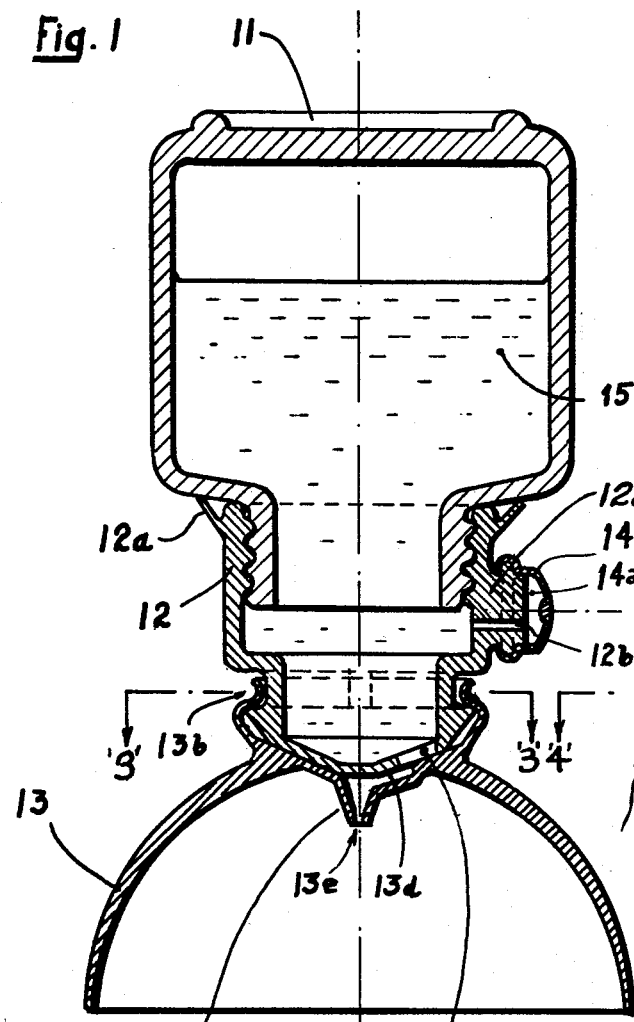
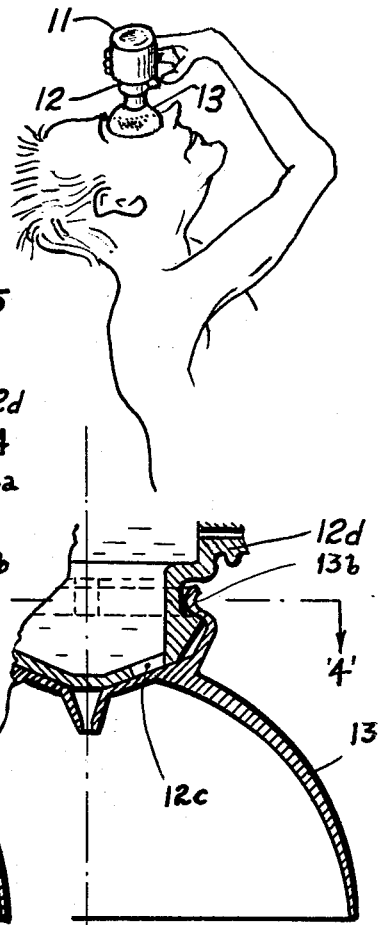
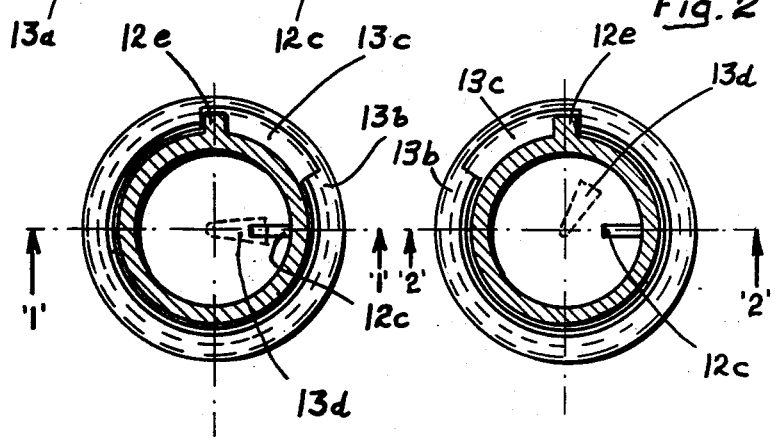

EYE DROP DISPENSER

This invention relates to devices which assist the application of medicated solutions to the eye without the aid of another person.

There are a good number of prescriptions requiring people, often elderly, to apply eye drops for prophylactic or therapeutic purposes. In hospitals this is done to a patient by a nurse, but elderly, unaided, people who often have lost a part of their natural skills have at times difficulty in applying an exact number of drops to the eye. As a consequence, the medicine is applied either not at all or excessively.

It was known to use tubular probes that can be dipped into the bottle containing the solution; a quantity is sucked into the probe and then pressed out when applied to the eye. However, such a method can lead to infections if the probes are not cleaned carefully and not kept in a sterilized surroundings. This is a further disadvantage of the conventional method: that it is not hygienic. Accordingly, one object of the invention is to provide a bottle cap which apart from serving as a closure also serves for dispensing the liquid, drop by drop, responsive to manual control.

Another object is to combine with the bottle cap a second cap usually a cup-like attachment acting as a slide valve which has two main positions, in one of which drops can be dispensed whereas in the other, the bottle interior is fully sealed off from the surroundings.

An important object is also to shape the cup-like attachment in such a way that by placing it on cheeks, nose and eye brows, it serves as a support and acts as a convenient locating device ensuring that the drops reach the eye.

These and other objects of the invention will become evident from the following description and the accompanying drawing wherein:

FIG. 1 is a cross section of the assembled device in its open position;

FIG. 2 is a partial section of the same device when in the closed position;

FIG. 3 is a sectional view through 3—3 of FIG. 1.

FIG. 4 is a sectional view through 4—4 of FIG. 2.

FIG. 5 is a perspective view of a person using the invention.

Referring now to FIG. 1 in detail, 11 is the bottle containing the medicated fluid 15, 12 is a cap for example made of plastic material, 12a is a thin flange which bears against the bottle 11 when the cup 12 is fully screwed onto the bottle. This flange provides a seal to prevent any air from entering the bottle through untight screw turns on the neck of the bottle. A nipple 12d which is integrally molded with the cap 12 has a hole 12b. A rubber hood 14 is placed over said nipple, which can be used as a button for temporarily reducing the volume 14d it encloses.

Furthermore, a second cap, more particularly a transparent cup-like part 13 is snapped over bottle cap 12, at 13b. The cup also has a nozzle 13e and groove 13d.

The cup 13 can be turned between two end positions about 60° apart. The cut-out 13c in the bend 13b determines the maximum angle by which cup 13 can be turned against stop 12e.

In one end position the aperture (orifice) 12c coincides with the duct portion 13d in the cup 13, FIG. 1. In the other position, the orifice 12c is covered and shut off. See FIG. 2 and FIG. 4.

The device according to the invention works as follows:

Assume the bottle 11 has just been filled with liquid 15, the cap 12 has been screwed on and the cup 13 turned to its "open" position, the whole device is then turned around and held downwards against the eye as illustrated in FIG. 5. No liquid can escape through the duct 13d because of the inability of the air volume above the liquid to expand without reducing its pressure. A certain quantity of air 14d is trapped inside the button 14. The volume of this air is slightly larger than the volume of one drop of liquid. By pushing button 14 the said air volume is displaced through duct 12b and rises to the top of the liquid in accordance with the law of Archimedes which says; that the bouyancy of any particle or solid body in a fluid is equal to the weights of the displaced volume minus the weights of that particle or body. Since water is much heavier than air, the latter rises in the form of bubbles. This addition to the upper air volume would increase its pressure which, however, is at once normalized by the release of one drop of liquid through the orifice 12c and duct 13d. The same is now released onto the eye of the user. As the pressure of the thumb on the button 14 is released, liquid is drawn through channel 12b into the space 14a. This causes a suction movement which reduces the air pressure above the liquid and, as a consequence, external air is admitted to the extent needed to replenish the air pressure in the bottle and to establish balance. The admission of air can, of course, only occur through nozzle 13e. When the person using the device pushes the button 14 a second time, the liquid now filling space 14a will be pumped through duct 12b and, for the balance of pressure to remain, one drop of liquid must be ejected from the bottle which can only pass through nozzle 13e.

It is easily seen that the patient can dispense an exact number of drops on the eye and has complete manual control over this process.

When the treatment of the eye is completed, the cup 13 is turned to the closure position to prevent contact with contaminating elements. The cup 13 can be readily detached for sterilizing if needed, and then put back in position again.

While various changes may be made in the detail construction it is understood that such changes will be within the spirit and scope of the present invention as is defined by the appended claims.

What is claimed is:

1. A device for accurately dispensing measured drops of liquid into a users eye, comprising a container having an open end and a hollow dispenser removably mounted axially exteriorly on said open end of the container in combination with a cup rotatably mounted axially on an opposite end of said dispenser having a portion adapted to fit around the users eye, said cup and dispenser having transverse relatively movable sealing surfaces including an axial orifice through said cup and an aperture in said dispenser sealing surface whereby said orifice registers with said aperature in one position to provide communication from the container into the cup, including a hollow member mounted on the external surface of said dispenser, longitudinally between the container and said cup, with a channel provided through the side wall of the dispenser providing communication from the interior of said member of said dispenser adjacent said container end, said member being flexible whereby manual pressure on said member will eject a measured drop from the container through the dispenser, the orifice and to the users eye, when the said aperture and orifice are orifice are in registry.

2. A device as in claim 1 wherein said cup includes a radial groove in communication with said orifice, and wherein said aperture is radially disposed extending from the side wall of the dispenser towards the axis thereof, and wherein the hollow member is a flexible button sealingly mounted on an external transverse projection from the dispenser, said projection having a flat surface oppossing the button thereby enclosing a predetermined volume there between.

* * * * *